(12) United States Patent
Rudolph et al.

(10) Patent No.: US 8,613,910 B2
(45) Date of Patent: Dec. 24, 2013

(54) FLAVONOIDS AS SYNERGISTS FOR ENHANCING THE ACTION OF SELF-TANNING SUBSTANCES

(75) Inventors: Thomas Rudolph, Darmstadt (DE); Herwig Buchholz, Frankfurt (DE); Jerzy Meduski, Fourqueux (FR)

(73) Assignee: Merck Patent GmbH, Darmstadt (DE)

( * ) Notice: Subject to any disclaimer, the term of this patent is extended or adjusted under 35 U.S.C. 154(b) by 496 days.

(21) Appl. No.: 11/996,846

(22) PCT Filed: May 10, 2006

(86) PCT No.: PCT/EP2006/004384
§ 371 (c)(1),
(2), (4) Date: Jan. 25, 2008

(87) PCT Pub. No.: WO2007/012356
PCT Pub. Date: Feb. 1, 2007

(65) Prior Publication Data
US 2008/0279793 A1     Nov. 13, 2008

Related U.S. Application Data

(60) Provisional application No. 60/702,983, filed on Jul. 28, 2005, provisional application No. 60/748,588, filed on Dec. 9, 2005.

(30) Foreign Application Priority Data

Jul. 27, 2005   (DE) .................... 10 2005 035 683

(51) Int. Cl.
*A61K 8/73*     (2006.01)
*A61Q 19/04*    (2006.01)
*A61K 9/70*     (2006.01)

(52) U.S. Cl.
USPC .............. 424/59; 424/443; 424/74; 424/750; 424/756; 424/746; 442/123

(58) Field of Classification Search
USPC .................... 424/59, 443, 74, 750, 756, 764; 442/123
See application file for complete search history.

(56) References Cited

U.S. PATENT DOCUMENTS

| | | | |
|---|---|---|---|
| 3,639,444 A | 2/1972 | Wessendorf | |
| 6,146,617 A * | 11/2000 | Kurz et al. ....................... | 424/59 |
| 6,235,721 B1 * | 5/2001 | Ghosal ............................. | 514/25 |
| 6,399,046 B1 * | 6/2002 | Schonrock et al. ............. | 424/59 |
| 6,406,682 B1 | 6/2002 | Martin et al. | |
| 2001/0046479 A1 | 11/2001 | Landa | |
| 2003/0138387 A1 | 7/2003 | Seyler et al. | |
| 2004/0126342 A1 * | 7/2004 | Dicianna ......................... | 424/59 |
| 2004/0191208 A1 * | 9/2004 | Courtin ........................... | 424/74 |
| 2004/0228810 A1 | 11/2004 | Hamson et al. | |
| 2005/0002994 A1 * | 1/2005 | Goppel et al. ................ | 424/443 |
| 2007/0196289 A1 | 8/2007 | Blatt et al. | |
| 2008/0199414 A1 * | 8/2008 | Wirth et al. .................... | 424/59 |

FOREIGN PATENT DOCUMENTS

| | | | | |
|---|---|---|---|---|
| EP | 0671159 A | 9/1995 | | |
| EP | 1092415 A | 4/2001 | | |
| EP | 1477159 A | 11/2004 | | |
| FR | 2831439 A | 5/2003 | | |
| GB | 2333772 A | 8/1999 | | |
| JP | 95 101848 | 7/1998 | | |
| WO | WO-94 04130 | 3/1994 | | |
| WO | WO-94 23693 | 10/1994 | | |
| WO | WO 99/66897 A | 12/1999 | | |
| WO | WO-01 03665 | 1/2001 | | |
| WO | WO 02/069926 A1 * | 9/2002 | ............. | A61K 7/48 |
| WO | WO 03/026605 A2 * | 4/2003 | ............. | A61K 7/48 |
| WO | WO 03/039492 A1 * | 5/2003 | ............. | A61K 7/00 |
| WO | WO-2005 027866 | 3/2005 | | |

OTHER PUBLICATIONS

"Catechin", Wikipedia [online]. [Retrieved on Jan. 3, 2011]. Retrieved from http://en.wikipedia.org/wiki/catechin.*
"Definition of including": Morris, William "The American Heritage Dictionary", 2nd College Edition, Boston, Houghton Mifflin Company, 1982.*
"Quercetin-induced melanogenesis in a reconstituted three-dimensional human epidermal model"; Journal of Molecular Histology; 2004; pp. 157-165; vol. 35.
"Influence of Hydration on Dihydrosyacetone-Induced Pigmentation of Stratum Corneum"; The Society for Investigative Dermatology, Inc.; 0022-202X/03; pp. 655-661.
Patent Abstracts of Japan Bd. 018, Nr. 061 (C-1160) Feb. 2, 1994—& JP 05279225A Suntory Ltd.
Patent Abstracts of Japan; "Tanning-Stimulating Cosmetic Composition"; Pub. No. 05-279225, Oct. 26, 1993; Suntory Ltd.
Patent Abstracts of Japan; "Melanine Production-Promoting Agent and Composition of External Preparation Used for Skin Containing the Same"; Pub. No. 2004-002264, Jan. 8, 2004; Tokai Univ.
Toyota Motor Corp, "Controller for vehicle lockup clutch," Patent Abstracts of Japan, Publication Date: Jul. 14, 1998; English Abstract of JP-10 184895.

* cited by examiner

*Primary Examiner* — Ernst Arnold
*Assistant Examiner* — Hong Yu
(74) *Attorney, Agent, or Firm* — Millen, White, Zelano, Branigan, P.C.

(57)  ABSTRACT

The invention relates to the use of at least one flavonoid having an uncharged flavan skeleton as synergist for enhancing the action of self-tanning substances, such as trioses and tetroses, in cosmetic and dermatological formulations and to corresponding novel compositions and to the preparation thereof.

26 Claims, No Drawings

FLAVONOIDS AS SYNERGISTS FOR ENHANCING THE ACTION OF SELF-TANNING SUBSTANCES

This application claims the benefit of the filing date of U.S. Provisional Application Ser. No. 60/702,983 filed Jul. 28, 2005, and U.S. Provisional Application Ser. No. 60/748,588 filed Dec. 9, 2005, both of which are incorporated by reference herein.

The present invention relates to the use of flavonoids having an uncharged flavan skeleton as synergists for enhancing the action of self-tanning substances in cosmetic and dermatological formulations, and to corresponding novel compositions, and to the preparation thereof.

The trend away from fashionable paleness to "healthy, sportily brown skin" has been uninterrupted for years. In order to achieve this, people expose their skin to sunlight since this causes a pigmentation in the sense of melanin formation. However, the UV radiation of sunlight also has a damaging effect on the skin. Besides acute damage (sunburn), long-term damage occurs, such as an increased risk of skin cancer to illness on excessive irradiation with light from the UVB region (wavelength 280-320 nm). In addition, excessive exposure to UVB and UVA radiation (wavelength: 320-400 nm) results in a weakening of the elastic and collagenic fibres of the connective tissue. This results in numerous phototoxic and photoallergic reactions and results in premature skin ageing.

Natural protection against the adverse consequences of sunlight is offered by tanning (pigmentation) of the skin. In its lowermost layer, the basal layer, the epidermis contains individual pigment-forming cells, the melanocytes, in addition to the basal cells. UV light stimulates the production of melanin in these cells, which is transported into the keratinocytes, where it becomes visible as a brown skin colour.

This pigment formation starting from the amino acid tyrosine is initiated predominantly by UVB radiation and is referred to as "indirect pigmentation". Its development proceeds over a number of days; the resultant tan lasts for a few weeks. In the case of "direct pigmentation", which commences with solar irradiation, predominantly colourless melanin precursors are oxidised by UVA radiation to dark-coloured melanin. Since this oxidation is reversible, it results in skin tanning which only lasts briefly.

Artificial tanning of the skin can be produced externally with the aid of make-up and orally by taking carotenoids.

Much more popular, however, is artificial tanning of the skin which can be achieved by application of so-called self-tanning agents, as are the subject-matter of the present invention. These compounds have, as chemical structural feature, keto or aldehyde groups in the vicinity of alcohol functions. These ketols or aldols belong predominantly to the sugars class of substances. A self-tanning substance which is employed particularly frequently is 1,3-dihydroxyacetone (DHA).

The compounds can be reacted with the proteins and amino acids of the horny layer of the skin in the sense of a Maillard reaction, where a reaction route which has not yet been fully clarified results in polymers which provide the skin with a brownish hue. This reaction is complete after about 4 to 6 hours. The tan achieved in this way cannot be washed off and is only removed with the normal skin desquamation.

The object of the present invention was accordingly to overcome disadvantages of the prior art and to find ways of providing cosmetic and dermatological self-tanning formulations which exhibit a stronger and longer-lasting action than the known tanning agents.

The use of flavonoids in cosmetics and dermatology is known per se. Thus, DE 19739349 describes the use of troxerutin as antioxidant or free-radical scavenger in cosmetic and dermatological compositions.

It is likewise known that trioses and tetroses, in particular DHA and erythrulose, are used as self-tanning substances in cosmetics.

Thus, EP 1 172 090 describes skin colouring compositions comprising DHA and a flavylium salt. Flavylium salts belong to the group of the anthocyanidines, which are not the subject-matter of the flavonoids used in accordance with the invention.

EP 1 092 415 discloses cosmetic and dermatological light-protection formulations which comprise DHA.

EP 1 277 461 discloses cosmetic formulations which comprise DHA as self-tanning substance.

EP 1 477 159 A1 discloses water-containing cosmetic compositions which comprise one or more self-tanning substances (such as DHA) and at least one phyllosilicate and further assistants and additives.

WO 2005/004826 discloses the use of a cosmetic composition which comprises at least one self-tanning substance (such as DHA) for matching the colour of skin areas pigmented differently.

Surprisingly, it has now been found that at least one flavonoid having an uncharged flavan skeleton can be used as synergist for enhancing the action of self-tanning substances in cosmetic and dermatological formulations. For the purposes of this invention, the term "flavonoid" encompasses substances whose flavan skeleton does not have a positive charge.

Preference is given here to the use of flavonoids which have a carbonyl function in the C4 position and an OH function in the C5 position of the flavan skeleton.

Self-tanning substances which can be employed are, inter alia:

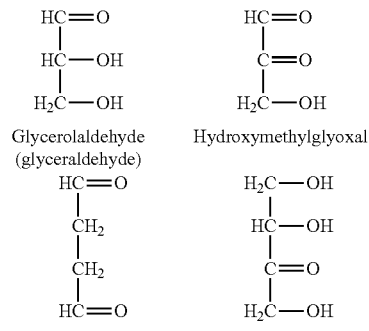

Glycerolaldehyde   Hydroxymethylglyoxal   γ-Dialdehyde   Erythrulose (glyceraldehyde)

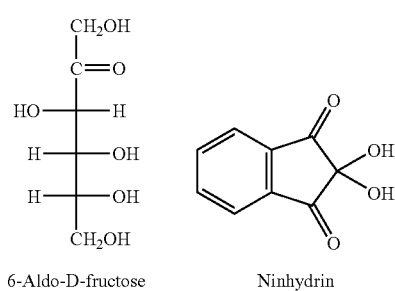 [SMILES: O=C(CO)C(O)C(O)C(O)CO ; O=C1c2ccccc2C(=O)C1(O)O]

Mention should furthermore be made of 5-hydroxy-1,4-naphthoquinone (juglone), which is extracted from the shells of fresh walnuts

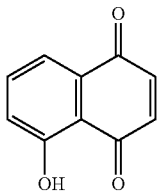 [SMILES: O=C1C=CC(=O)c2c(O)cccc21]

5-Hydroxy-1,4-naphthoquinone (juglone)
and 2-hydroxy-1,4-naphthoquinone (lawsone), which occurs in henna leaves

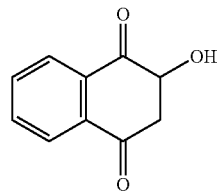 [SMILES: O=C1CC(O)C(=O)c2ccccc21]

2-Hydroxy-1,4-naphthoquinone (lawsone).

Preference is given to the use of the following trioses and tetroses:
1,3-diyhydroxyacetone (DHA), glyceraldehyde, dihydroxyacetone phosphate, glyceraldehyde phosphate, erythrose and 1,3,4-trihydroxy-2-butanone (erythrulose).

Very particular preference is given to erythrulose and 1,3-dihydroxyacetone (DHA), a trifunctional ketosugar which occurs in the human body, and derivatives thereof.

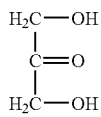

1,3-Dihydroxyacetone (DHA)

All compounds or components which can be used in the compositions are either known and commercially available or can be synthesised by known processes.

Use is made in accordance with the invention of flavonoids which can be assigned to the following groups owing to their basic structure:
chalcones
aurones
flavanones
flavan-3-ols (catechols)
flavones
isoflavones
flavan-3,4-diols (leukoanthocyanidines)
flavonols (3-hydroxyflavon-4-one)
flavanonols The name "flavonoid" is derived from the Latin word flavus=yellow and thus takes into account the fact that most of these substances have a yellowish colour in their pure form.

The following flavonoids should be mentioned by way of example: 5-hydroxy-7,4'-dimethoxyflavone 8-sulfate, 7,8-dihydroxyflavone, luteolin (flavone); catechol, epicatechol, epigallocatechol gallate (EGCG, TEAVIGO® DSM) (flavan-3-ols or flavan-3-ol derivatives); kaempferol (flavonol); taxifolin (flavanonol).

Preferred flavonoids are derived from the following groups:
flavonols
flavonol o-glycosides
flavonol o-glycoside-containing extracts Flavonoids usually occur as soluble glycosides in the cell sap of plants. The preferred flavonoids also include aglycones (sugar-free structures) and aglycone conjugates. Possible aglycone conjugates are hydroxyl derivatives, where all or some of the hydroxyl groups are alkylated, methylated, glycylated, sulfated or esterified. Besides hydroxyl derivatives, C derivatives are also suitable as aglycone conjugates.

For the group of the flavonols, particular preference is given to the aglycone quercetin.

In the group of the flavonol o-glycosides, the flavonol 3-glycosides, such as rutin, α-glucosylrutin, tiliroside, isoquercetin, rutin sulfate, trishydroxyethylrutin (troxerutin), and sulfates and phosphates thereof are particularly preferred. Even more preferred are rutin sulfate and troxerutin. The term "rutin sulfate" encompasses mono-, di-, tri-, tetra- or polysulfates of rutin and mixtures of these rutin sulfates. The term "troxerutin" encompasses mono-, di-, tri-, tetra- or polyethoxylates of rutin and mixtures of these rutin ethoxylates.

Flavonol 7- and -8-glycosides can also be used.

For the group of the flavonol or flavonol o-glycoside-containing extracts, the active ingredient combinations emblica, liquorice and/or horse chestnut extract are preferred. Emblica is obtained from the fruit of the deciduous tree Phyllanthus emblica (also Emblica officinalis), for example in India, China, Pakistan or Nepal. The principal ingredients of emblica are the low-molecular-weight tannic acids emblicanin A and B, which bind the iron occurring in the skin in the form of complexes. Preferred emblica solutions are commercially available, for example as EMBLICA® (MERCK) or CAPROS® (see, for example, U.S. Pat. No. 6,235,721 or U.S. Pat. No. 6,124,268). In principle, all emblica mixtures are suitable for combination with the self-tanning substances and flavonoids to be employed in accordance with the invention. The liquorice extract contains the flavonoid glabridin (a stearyl glycyrhetinate). The horse chestnut extract contains, for example, esculin and other flavonol and/or flavonol glycoside constituents.

Plant substance mixtures of this type can be obtained in a manner familiar to the person skilled in the art, for example by pressing or extraction of the corresponding plants.

The flavonoid is preferably employed in the cosmetic or dermatological formulation in a total amount of 0.01 to 10% by weight, more preferably in an amount of 0.1 to 5% by weight.

In the tanning reaction, a distinction is made, as already mentioned above, between direct and indirect reaction. The tanning reaction by means of trioses and tetroses is based on a direct, non-enzymatic reaction which proceeds analogously to the known Maillard reaction. It is initiated by UVA radiation and results in direct darkening of the skin pigments. The said substances react as ketoses with proteins of the skin to give brown-yellow coloured products, the so-called melanoids. However, these coloured products do not themselves have UV-absorbing properties, and consequently additional sun protection (clothing, hat, UV filter) is necessary on exposure to the sun.

By contrast, the indirect tanning process is enzyme-controlled (by the enzyme tyrosinase) and is initiated by UVB radiation. It is furthermore known that some chemical active ingredients are capable of activating tyrosinase and can thus indirectly increase the production of melanin. This effect was recently demonstrated for quercetin. (J. of Mol. Histology. 35:157-165 (2004); Pigment Cell Res. 17: 66-73 (2004))

Tanning caused directly by triose and/or tetrose takes place rapidly (within hours), while indirect tanning by quercetin takes a few days.

It was thus not foreseeable that flavonoids (for example quercetin) exhibit a synergistic effect in direct skin tanning if they are combined with a triose (for example DHA) or a tetrose (for example erythrulose). This advantageous effect has been demonstrated by the following Maillard test using the example of DHA in combination with quercetin:

Trial solutions of DHA with lysine with or without quercetin were prepared in an ethylene glycol/water mixture. Depending on whether oxygen was present or not, DHA exhibited different reaction behaviour.

In the absence of oxygen, DHA reacted with lysine to give a dark-brown solution.

In the presence of oxygen, however, DHA reacted with a yellow colour, unless quercetin was present, since the colour then changed to brown. It is thus assumed that quercetin is able to prevent the rapid decomposition of DHA in the presence of oxygen.

Maillard test systems used are described in B. Nguyen et al., J. Invest. Dermatol. 120 (2003), 655-661.

The composition according to the invention, which combines a self-tanning substance and a flavonoid, has the following advantages over a self-tanning product without addition of flavonoid:

- stabilisation of the triose or tetrose against oxygen (on the skin and in the product)
- acceleration of the tanning reaction
- extension of the tanning reaction due to the indirect tanning reaction (UV-free tanning extension)
- enhancement of the tanning reaction
- composition according to the invention comes close to natural tanning All flavonoids tested in accordance with the invention have a flavan skeleton which is not positively charged. It must be assumed that this is essential in order adequately to complex metal ions, such as, for example, $Fe^{2+}/Cu^{2+}$, on the skin. As a consequence, the self-tanning substance is protected against autoxidation. By contrast, a positively charged flavan skeleton, as present, for example, in anthocyanidines, is less suitable for this purpose.

The present invention furthermore relates to compositions which comprise at least one flavonoid having an uncharged flavan skeleton and at least one active sub-stance whose action is synergistically enhanced by the presence of the flavonoid. The active substance employed is preferably a self-tanning substance, such as trioses or tetroses.

The flavonoid employed for the compositions, as already described above, is preferably a flavonol, flavonol o-glycoside, flavonol- or flavonol o-glycoside-containing extracts.

The invention furthermore relates to compositions which comprise ethylenediaminetetraacetic acid (EDTA) and/or salts thereof (in particular sodium salts thereof) and/or other organic complexing agents, in particular EDTA derivatives, for example Titriplex® I-IV (see chemical reagents 2002, VWR International, Merck KGaA, pp. 982-984) and/or salts thereof (in particular sodium salts thereof) and/or ethylenediaminetetramethylenephosphonic acid and/or salts thereof (for example pentasodium ethylenediaminetetramethylenephosphonate) and a self-tanning substance, such as, for example, DHA.

Preference is also given to compositions which comprise Oxynex (such as, for example, Oxynex® AP, Oxynex® K LIQUID, Oxynex® L LIQUID, Oxynex® LM, Oxynex® 2004, Oxynex ST (see WO 03/007908)) and a self-tanning substance, such as, for example, DHA.

The compositions here are usually compositions which can be applied topically, for example cosmetic or dermatological formulations. In this case, the compositions comprise a cosmetically or dermatologically suitable vehicle and, depending on the desired property profile, optionally further suitable ingredients.

The invention furthermore relates to a process for the preparation of a composition in which at least one flavonoid and at least one active substance (for example triose, such as DHA) are mixed successively on the skin or applied successively to the skin with a cosmetically or dermatologically suitable carrier.

This mixing process is preferably carried out with the aid of a two-chamber bottle. Preference is likewise given to a process in which the mixing or application of the composition according to the invention to the skin is carried out by firstly rinsing with a flavonoid solution and subsequently with a DHA solution.

The present invention additionally relates to the use of a composition according to the invention for topical use or for use on a surface.

The active substances to be employed in accordance with the invention furthermore include, for example, UV filters, flavone derivatives, chromone derivatives, aryl oximes and parabens.

Parabens are 4-hydroxybenzoic acid esters which are used in free form or as sodium salts for the preservation of compositions in the area of foods, cosmetics and medicaments. The action of the esters is directly proportional to the chain length of the alkyl radical, but on the other hand the solubility decreases with increasing chain length. As non-dissociating compounds, the esters are predominantly pH-independent and act in a pH range from 3.0-8.0. The antimicrobial action mechanism is based on damage of the microbe membranes by the surface activity of the PHB esters and on protein denaturing. In addition, interactions occur with coenzymes. The action is directed against fungi, yeasts and bacteria. The most important parabens as preservatives are methyl 4-hydroxybenzoate, ethyl 4-hydroxybenzoate, propyl 4-hydroxybenzoate and butyl 4-hydroxybenzoate.

Of the aryl oximes, preference is given to the use of 2-hydroxy-5-methyllaurophenone oxime, which is also known as HMLO, LPO or F5. Its suitability for use in cosmetic compositions is disclosed, for example, in DE 41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and other allergic and/or inflammatory diseases of the skin and skin appendages. Compositions according to the invention which, in addition to the said compound(s), additionally comprise an aryl oxime, preferably 2-hydroxy-5-methyllaurophenone oxime, exhibit surprising anti-inflammatory suitability. The compositions here preferably comprise 0.01 to 10% by weight of the aryl oxime, it being particularly preferred for the composition to comprise 0.05 to 5% by weight of aryl oxime.

For the purposes of the invention, flavone derivatives are taken to mean flavonoids and coumaranones. Of the coumaranones, 4,6,3',4'-tetrahydroxybenzylcoumaranone-3 is preferred.

Chromone derivatives are preferably taken to mean certain chromen-2-one derivatives which are suitable as active ingredients for the preventative treatment of human skin and human hair against ageing processes and damaging environmental influences. They simultaneously exhibit a low irritation potential for the skin, have a positive effect on water binding in the skin, maintain or increase the elasticity of the skin and thus promote smoothing of the skin. These compounds preferably conform to the following formula

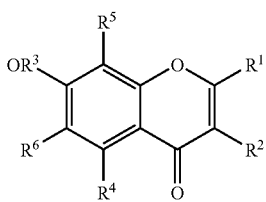

where
$R^1$ and $R^2$ may be identical or different and are selected from
H, —C(=O)—$R^7$, —C(=O)—$OR^7$,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3,
$R^3$ stands for H or straight-chain or branched $C_1$- to $C_{20}$-alkyl groups,
$R^4$ stands for H or $OR^8$,
$R^5$ and $R^6$ may be identical or different and are selected from
—H, —OH,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and
$R^7$ stands for H, straight-chain or branched $C_1$- to $C_{20}$-alkyl groups, a polyhydroxyl compound, such as, preferably, an ascorbic acid radical or glycosidic radicals, and
$R^8$ stands for H or straight-chain or branched $C_1$- to $C_{20}$-alkyl groups,
where at least 2 of the substituents $R^1$, $R^2$, $R^4$-$R^6$ are different from H or at least one substituent from $R^1$ and $R^2$ stands for —C(=O)—$R^7$ or —C(=O)—$OR^7$.

The proportion of one or more compounds selected from flavonoids, chromone derivatives and coumaranones in the composition according to the invention is preferably 0.001 to 5% by weight, particularly preferably 0.01 to 2% by weight, based on the composition as a whole.

The protective action of compositions according to the invention against oxidative stress or against the action of free radicals can be improved if the compositions comprise one or more antioxidants, where the person skilled in the art is presented with absolutely no difficulties in selecting antioxidants which act suitably quickly or in a delayed manner.

In a preferred embodiment of the present invention, the composition according to the invention is therefore a composition for the protection of body cells against oxidative stress, in particular for reducing skin ageing, characterised in that it comprises one or more antioxidants besides the flavonoids and the self-tanning sub-stances and optionally other ingredients.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to pmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Anti-oxidants of this type are usually employed in such compositions with the compounds according to the invention in ratios in the range from 1000:1 to 1:1000, preferably in amounts of 100:1 to 1:100.

The compositions to be employed in accordance with the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. Vitamins are usually employed in such compositions with the compounds according to the invention in ratios in the range from 1000:1 to 1:1000, preferably in amounts of 100:1 to 1:100.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers and I. M. C. M. Rietjens (Free Radical Biology&Medicine 2001, 31(7), 869-881), are investigating the pH dependence of the antioxidant action of hydroxyflavones. Quercetin exhibits the greatest activity amongst the structures investigated over the entire pH range.

Suitable antioxidants are furthermore compounds of the formula (III)

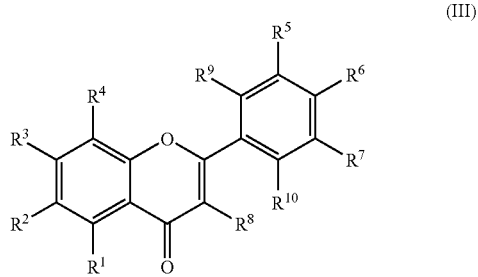

(III)

where $R^1$ to $R^{10}$ may be identical or different and are selected from
H
$OR^{11}$
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3, where all $OR^{11}$, independently of one another, stand for OH
straight-chain or branched $C_1$- to $C_{20}$-alkoxy groups,
straight-chain or branched $C_3$- to $C_{20}$-alkenyloxy groups,
straight-chain or branched $C_1$- to $C_{20}$-hydroxyalkoxy groups, where the hydroxyl group(s) may be bonded to a primary or secondary carbon atoms of the chain and furthermore the alkyl chain may also be interrupted by oxygen, and/or
$C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or
mono- and/or oligoglycosyl radicals,
with the proviso that at least 4 radicals from $R^1$ to $R^7$ stand for OH and that at least 2 pairs of adjacent —OH groups are present in the molecule,
or $R^2$, $R^5$ and $R^6$ stand for OH and the radicals $R^1$, $R^3$, $R^4$ and $R^{7-10}$ stand for H,
as described in German patent application DE-A-102 44 282.

Advantages of the compositions according to the invention comprising at least one antioxidant, besides the above-mentioned advantages, are, in particular, the antioxidant action and the good tolerance by the skin. Particularly advantageous is the particular action profile of the compounds of the formula (III), which is evident in the DPPH assay from a high capacity for scavenging free radicals ($EC_{50}$), a delayed action ($T_{EC50}$>120 min) and thus moderate to high anti-free-radical efficiency (AE). In addition, the compounds of the formula (III) combine in the molecule antioxidative properties with UV absorption in the UV-A and/or -B region. Preference is therefore also given to compositions comprising at least one compound of the formula (III) which is characterised in that at least two adjacent radicals of the radicals $R^1$ to $R^4$ stand for OH and at least two adjacent radicals of the radicals $R^5$ to $R^7$ stand for OH. Particularly preferred compositions comprise at least one compound of the formula (III) which is characterised in that at least three adjacent radicals of the radicals $R^1$ to $R^4$ stand for OH, where the radicals $R^1$ to $R^3$ preferably stand for OH.

Compositions which are particularly preferred in accordance with the invention can also serve for sun protection and then also comprise UV filters in addition to the flavonoids and the self-tanning substances and optionally other ingredients.

In principle, all UV filters are suitable for combination with the self-tanning sub-stances and flavonoids to be employed in accordance with the invention. Particular preference is given to UV filters whose physiological acceptability has already been demonstrated. Both for UVA and UVB filters, there are many proven sub-stances which are known from the specialist literature, for example benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL), benzoyl- or dibenzoylmethanes, such as 1-(4-tert-butylphenyl)-3-(4-methoxyphenyl)propane-1,3-dione (for example Eusolex® 9020) or 4-isopropyldibenzoylmethane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex®

2292) or isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007) or ethoxylated ethyl 4-aminobenzoate (for example Uvinul® P25), phenylbenzimidazolesulfonic acids, such as 2-phenylbenzimidazole-5-sulfonic acid and the potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;

and further substances, such as 2-ethylhexyl 2-cyano-3,3-diphenylacrylate (for example Eusolex® OCR), 3,3'-(1,4-phenylenedimethylene)bis(7,7-dimethyl-2-oxobicyclo[2.2.1]hept-1-ylmethanesulfonic acid and salts thereof (for example Mexoryl® SX) and 2,4,6-trianilino-(p-carbo-2'-ethylhexyl-1'-oxy)-1,3,5-triazine (for example Uvinul® T 150)

hexyl 2-(4-diethylamino-2-hydroxybenzoyl)benzoate (for example Uvinul® UVA Plus, BASF).

The compounds mentioned in the list should only be regarded as examples. It is of course also possible to use other UV filters.

Further suitable organic UV filters are, for example, 2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®), 2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), α-(trimethylsilyl)-ω-[trimethylsilyloxy]poly[oxy(dimethyl) [and about 6% of methyl[2-[p-[2,2-bis(ethoxycarbonyl) vinyl]phenoxy]-1-methyleneethyl] and about 1.5% of methyl[3-[p-[2,2-bis(ethoxycarbonyl)vinyl]phenoxy)propenyl) and 0.1 to 0.4% of (methylhydrogen)silylene]] (n≈60) (CAS No. 207 574-74-1)

2,2'-methylenebis(6-(2H-benzotriazol-2-yl)-4-(1,1,3,3-tetramethylbutyl)phenol) (CAS No. 103 597-45-1)

2,2'-(1,4-phenylene)bis(1H-benzimidazole-4,6-disulfonic acid, monosodium salt) (CAS No. 180 898-37-7) and 2,4-bis{[4-(2-ethylhexyloxy)-2-hydroxy]phenyl}-6-(4-methoxyphenyl)-1,3,5-triazine (CAS No. 103 597-45-, 187 393-00-6).

Further suitable UV filters are also methoxyflavones corresponding to the earlier German patent application DE-A-10232595.

Organic UV filters are generally incorporated into cosmetic formulations in an amount of 0.5 to 20 percent by weight, preferably 1-15%.

In order to ensure optimised UV protection, it is furthermore preferred for compositions having light-protection properties also to comprise inorganic UV filters. Conceivable inorganic UV filters are those from the group of the titanium dioxides, such as, for example, coated titanium dioxide (for example Eusolex® T-2000, Eusolex® T-AQUA, Eusolex® T-AVO), zinc oxides (for example Sachtotec®), iron oxides or also cerium oxides. These inorganic UV filters are generally incorporated into cosmetic compositions in an amount of 0.5 to 20 percent by weight, preferably 2-10%.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and the potassium, sodium and triethanolamine salts thereof.

The protective action against damaging effects of UV radiation can be optimised by combining one or more of the said compounds having a UV-filter action.

Optimised compositions may comprise, for example, the combination of the organic UV filters 4'-methoxy-6-hydroxyflavone with 1-(4-tert-butylphenyl)-3-(4-methoxyphenyl) propane-1,3-dione and 3-(4'-methylbenzylidene)-dl-camphor. This combination gives rise to broad-band protection, which can also be supplemented by the addition of inorganic UV filters, such as titanium dioxide microparticles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin are repeatedly discussed in the literature. The encapsulation of the corresponding substances which is proposed here suppresses this effect.

In general, encapsulation of individual UV filters or other ingredients enables preparation problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions to be employed in accordance with the invention are preferably present in amounts which ensure that the encapsulated UV filters are present in the composition in the above-indicated amounts.

The compositions to be employed in accordance with the invention may in addition comprise further conventional skin-protecting or skin-care active ingredients. These may in principle be all active ingredients known to the person skilled in the art.

Particularly preferred active ingredients are, for example, also so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and the respective precursors thereof. For the purposes of German patent application DE-A-10133202, osmolytes are taken to mean, in particular, substances from the group of the polyols, such as, for example, myo-inositol, mannitol or sorbitol and/or one or more of the osmolytically active substances mentioned below:
taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

In accordance with the invention, compatible solutes are preferably substances selected from the group consisting of pyrimidinecarboxylic acids (such as ectoine and hydroxyectoine), proline, betaine, glutamine, cyclic diphosphoglycerate, N-acetylornithine, trimethylamine N-oxide, di-myo-inositol phosphate (DIP), cyclic 2,3-diphosphoglycerate (cDPG), 1,1-diglycerol phosphate (DGP), β-mannosyl glycerate (firoin), β-mannosylglyceramide (firoin A) or/and dimannosyl diinositol phosphate (DMIP) or an optical isomer, derivative, for example an acid, or a salt or ester of these compounds, or combinations thereof.

Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutically active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-up, care creams and sunscreen preparations.

Preference is given here to the use of a pyrimidinecarboxylic acid of the following formula

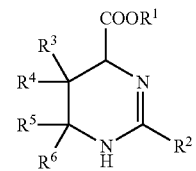

in which $R^1$ is a radical H or C1-8-alkyl, $R^2$ is a radical H or C1-4-alkyl, and $R^3$, $R^4$, $R^5$ and $R^6$ are each, independently of one another, a radical from the group H, OH, $NH_2$ and C1-4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid). The compositions to be employed in accordance with the invention preferably comprise pyrimidinecarboxylic acids of this type in amounts of up to 15% by weight.

It is particularly preferred in accordance with the invention for the compatible solutes to be selected from di-myo-inositol phosphate (DIP), cyclic 2,3-diphosphoglycerate (cDPG), 1,1-diglycerol phosphate (DGP), β-mannosyl glycerate (firoin), β-mannosylglyceramide (firoin A) or/and dimannosyl diinositol phosphate (DMIP), ectoine, hydroxyectoine or mixtures thereof.

Of the aryl oximes likewise preferably employed, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and skin appendages. Compositions according to the invention which additionally comprise an aryl oxime, preferably 2-hydroxy-5-methyllaurophenone oxime, exhibit anti-inflammatory suitability. The compositions here preferably comprise 0.01 to 10% by weight of the aryl oxime, it being particularly preferred for the composition to comprise 0.05 to 5% by weight of aryl oxime.

The flavonoids which act as synergists and the self-tanning agents and optionally further active ingredients can be incorporated into cosmetic or dermatological compositions in the conventional manner. The compositions are preferably suitable for external use, for example as cream, lotion, gel or as solution which can be sprayed onto the skin. For oral use, administration forms such as capsules, dragees, powders, tablet solutions or solutions would be conceivable.

As use form of the compositions to be employed in accordance with the invention, mention may be made, for example, of: solutions, suspensions, emulsions, PIT emulsions, pastes, ointments, gels, creams, lotions, powders, soaps, surfactant-containing cleansing preparations, oils, aerosols and sprays. Preferred use forms are shampoos, sun baths and shower baths, which are also known as spray tanning, airbrush tanning or sun showers from commercial self-tanning studios. Spray tanning, airbrush tanning or sun showers are actually the same, i.e., for example, a DHA solution (and further active substances) are applied to the body. The distinction lies merely in the execution.

Any desired conventional vehicles, assistants and optionally further active ingredients can be added to the compositions.

The invention furthermore relates to a kit consisting of a two-chamber system, preferably a two-chamber bottle, with pump device for the storage and provision of the composition according to the invention according to Claim 1, where the flavonoid and the self-tanning substance and further active substances and assistants are located in two separate chambers and are applied successively to the skin. Since, for example, natural vitamins are often unstable in cream bases, these could, for example, be stored in a two-chamber bottle separately from the cream base (for example a DHA emulsion) and only mixed directly on the skin. The efficacy of sensitive active ingredients (for example vitamins) is thereby retained.

Preferred assistants originate from the group of the preservatives, antioxidants, stabilisers, solubilisers, vitamins, colorants and odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

A further use form which may be mentioned is the two-chamber bottle in which bioflavonoid and self-tanning substance (for example DHA) are stored in two separate chambers and are applied to the skin successively by a plurality of pump shots and only there are mixed by the user. This has the advantage that particularly sensitive active ingredients, such as, for example, vitamins, which are unstable in many cream bases, can be stored separately from a cream base and are only added to the cream base by actuation of the dispenser on the bottle. The efficacy, for example of the vitamins, is thereby retained better.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lip-care sticks, powder, emulsion and wax make-up, and sunscreen, pre-sun and after-sun preparations.

The preferred composition forms according to the invention also include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
  mineral oils, mineral waxes;
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
  silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and waxes, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24 C atoms, in particular 12-18 C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The aqueous phase of the compositions to be employed in accordance with the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions to be employed in accordance with the invention comprise hydrophilic surfactants.

The hydrophilic surfactants are preferably selected from the group of the alkylglucosides, acyl lactylates, betaines and coconut amphoacetates.

It is likewise advantageous to employ natural or synthetic raw materials and assistants or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group of the substances which are distinguished by the structural formula

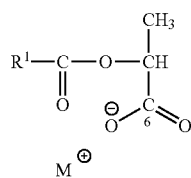

where $R^1$ denotes a branched or unbranched alkyl radical having 1 to 30 carbon atoms, and $M^+$ is selected from the group of the alkali metal ions and the group of the ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group of the substances which are distinguished by the structural formula

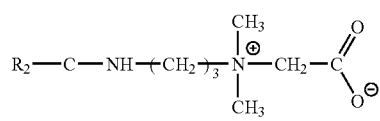

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageous in accordance with the invention is, for example, sodium coconut amphoacetate, as available under the name Miranol® Ultra C32 from Miranol Chemical Corp.

The compositions to be employed in accordance with the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A-43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols). Particular preference is given to the following: polyethylene glycol (13)

stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:
fatty alcohols having 8 to 30 carbon atoms, monoglycerol esters of saturated and/or unsaturated, branched and/or unbranched alkanecarboxylic acids having a chain length of 8 to 24 C atoms, in particular 12-18 C atoms, diglycerol esters of saturated and/or unsaturated, branched and/or unbranched alkanecarboxylic acids having a chain length of 8 to 24 C atoms, in particular 12-18 C atoms, monoglycerol ethers of saturated and/or unsaturated, branched and/or unbranched alcohols having a chain length of 8 to 24 C atoms, in particular 12-18 C atoms, diglycerol ethers of saturated and/or unsaturated, branched and/or unbranched alcohols having a chain length of 8 to 24 C atoms, in particular 12-18 C atoms, propylene glycol esters of saturated and/or unsaturated, branched and/or unbranched alkanecarboxylic acids having a chain length of 8 to 24 C atoms, in particular 12-18 C atoms, and sorbitan esters of saturated and/or unsaturated, branched and/or unbranched alkanecarboxylic acids having a chain length of 8 to 24 C atoms, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Preferred compositions in accordance with the invention are in various administration forms usually used for this application. For example, they may, in particular, be in the form of a lotion or emulsion, such as in the form of a cream or milk (O/W, W/O, O/W/O, W/O/W), in the form of oily/alcoholic, oily/aqueous or aqueous/alcoholic gels or solutions, in the form of solid sticks or preferably in the form of an aerosol and shower bath.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substances, a lower monoalcohol or lower polyol or mixtures thereof. Particularly preferred monoalcohols or polyols include ethanol, i-propanol, propylene glycol, glycerol and sorbitol.

A preferred embodiment of the invention is an emulsion in the form of a protective cream or milk which comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily/alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily/alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, preferably alkanes, are generally used.

Preference is furthermore given to compositions which consist merely of a premix of triose and/or tetrose and a flavonoid, where the mixing ratio is between 100:1 and 1:5. The mixing ratio of the triose premix to flavonoid is particularly preferably between 5:1 and 1:2. A triose (preferably troxerutin) premix to flavonoid (preferably DHA) of 2:1 is most preferred.

The compositions to be employed in accordance with the invention can be pre-pared with the aid of techniques which are well known to the person skilled in the art.

Even without further comments, it is assumed that a person skilled in the art will be able to utilise the above description in the broadest scope. The preferred embodiments should therefore merely be regarded as descriptive disclosure which is absolutely not limiting in any way. The complete disclosure content of all applications and publications mentioned above and below is incorporated into this application by way of reference.

The examples of the subject-matter according to the invention that are mentioned below serve merely for explanation and absolutely do not restrict the present invention in any way. In addition, the invention described can be carried out in the entire range claimed. All compounds or components which can be used in the compositions are either known and commercially available or can be synthesised by known methods. The INCI names of the raw materials used are indicated (the INCI names are by definition indicated in English).

EXAMPLE 1

Tanning-accelerating in-vivo action of troxerutin and rutin sulfate in DHA solutions
ITA° values (drop in the ITA° values compared with $t_0$)

|  | 2 h | 4 h | 24 h |
|---|---|---|---|
| Formulation A | −4.80 | −6.84 | −8.21 |
| Formulation B | −4.98 | −6.99 | −8.35 |
| Formulation C | −3.14 | −5.80 | −7.67 |

Formulations A, B and C each comprise 2% of dihydroxyacetone (DHA). Formulation A additionally comprises 1% of troxerutin, formulation B additionally comprises 1% of rutin sulfate. The investigation was carried out on 6 test subjects (forearm, application rate 2 mg cm$^{-2}$, difference from the untreated skin area). The measurements of the skin colour were carried out using the L*a*b* system ("Commission Internationale de l'Eclairage" [CIE Publication, 1986]). In order to evaluate the chromameter measurements, use was made, in particular, of the ITA° value, which best reflected the visual perception of the tanning enhancement (ITA° value=individual typologic angle; ITA°=[ArcTan(L*−50)/b*)]×180/π).

Compositions

Illustrative formulations of cosmetic compositions which comprise a flavonoid, for example rutin or troxerutin, and a self-tanning substance, for example DHA, are indicated below. In addition, the INCI names of the commercially available compounds are indicated. The DHA shower solutions are prepared by weighing all raw materials and stirring until homogeneous.

EXAMPLE 2

DHA Shower Solution

| INCI | [%] |
|---|---|
| Aqua (Water) | 75.05 |
| Dihydroxyacetone | 8.00 |
| Rutin | 0.75 |
| Ectoin | 0.30 |
| Propylene glycol | 4.50 |
| Glycerin | 2.00 |
| Ethoxydiglycol | 5.00 |
| Dimethyl isosorbide | 2.00 |
| Polysorbate 80 | 0.50 |
| Propylene glycol, walnut extract | 1.50 |
| Caramel | 0.10 |
| Parfum | 0.30 |

EXAMPLE 3

DHA Shower Solution

Composition analogous to Example 2, only with 0.75% of troxerutin employed instead of rutin.

EXAMPLE 4

Self-Tanning Cream Comprising Flavonoids (O/W)

The self-tanning cream is prepared by heating phase A (consisting of glyceryl stearate, stearyl alcohol, cetearyl alcohol, cetearyl ethylhexanoate, caprylic triglyceride, stearoxydimethicone, dimethicone, tocopheryl acetate and propylparaben) and phase B (consisting of propylene glycol, methylparaben and water). Phase B is slowly stirred into phase A, and the mixture is homogenised. The mixture is cooled with stirring. The rutin is dissolved in the water before the DHA. Phase C (consisting of DHA, rutin and water) is added at 40° C.

| INCI | [%] |
| --- | --- |
| Aqua (Water) | 69.00 |
| Dihydroxyacetone | 2.00 |
| Rutin | 1.00 |
| Methylparaben | 0.15 |
| Propylene glycol | 3.00 |
| Glyceryl stearate, Stearyl alcohol CETEH-20, STEARETH-25 | 8.00 |
| Cetearyl alcohol | 1.50 |
| Cetearyl ethylhexanoate | 6.50 |
| Caprylic/Capric triglyceride | 6.50 |
| Stearoxy dimethicone | 1.20 |
| Dimethicone | 0.50 |
| Tocopheryl acetate | 0.50 |
| Propylparaben | 0.05 |
| Parfum | 0.10 |

EXAMPLE 5

Self-Tanning Cream with Flavonoids (O/W)

Composition analogous to Example 4, only with 1% of troxerutin employed instead of rutin.

The invention claimed is:

1. A method for enhancing the action of a self-tanning substance in a cosmetic and/or dermatological formulation comprising including in said formulation a synergistically effective amount of at least one flavonoid having an uncharged flavan skeleton as synergist wherein said flavonoid is quercetin, rutin, rutin sulfate, troxerutin and/or isoquercetin and wherein said self-tanning substance is dihydroxyacetone or 1,3,4-trihydroxy-2-butanone (erythrulose) and wherein the ratio of self-tanning substance to flavonoid is from 5:1 to 1:2.

2. A method according to claim 1, wherein the flavonoid is quercetin.

3. A method according to claim 1, wherein the flavonoid is rutin sulfate and/or troxerutin.

4. A method according to claim 1, wherein the self-tanning substance is dihydroxyacetone.

5. A method according to claim 1, wherein the self-tanning substance is 1,3,4-trihydroxy-2-butanone (erythrulose).

6. A method according to claim 1, wherein the cosmetic or dermatological formulation comprises at least one flavonoid in a total amount of 0.01 to 10% by weight.

7. A method according to claim 1, wherein the cosmetic or dermatological formulation comprises at least one substance which absorbs UV radiation in the UV-A and/or UV-B region.

8. A method according to claim 1, wherein the cosmetic or dermatological formulation comprises an inorganic pigment which serves as a UV filter substance.

9. A cosmetic and/or dermatological composition comprising a self-tanning substance and at least one flavonoid having an uncharged flavan skeleton and at least one active substance whose action is synergistically enhanced by the presence of the flavonoid wherein said flavonoid is quercetin, rutin, rutin sulfate, troxerutin and/or isoquercetin, and wherein said self-tanning substance is dihydroxyacetone or 1,3,4-trihydroxy-2-butanone (erythrulose) and wherein the ratio of self-tanning substance to flavonoid is from 5:1 to 1:2.

10. A composition according to claim 9, wherein the flavonoid is quercetin.

11. A composition according to claim 9, wherein the flavonoid is rutin, rutin sulfate, troxerutin or isoquercetin.

12. A composition according to claim 11, wherein the flavonoid is rutin sulfate and/or troxerutin.

13. A composition according to claim 9, wherein the cosmetic or dermatological formulation comprises at least one flavonoid in a total amount of 0.01 to 10% by weight.

14. A composition according to claim 9, further comprising a UV filter, flavone derivative, chromone derivative, aryl oxime or a paraben.

15. A composition according to claim 9, further comprising one or more antioxidant, vitamin, DL-a-tocopherol, tocopherol E acetate, nicotinic acid, pantothenic acid or biotin.

16. A composition according to claim 9, where the composition, in addition to the at least one flavonoid and the at least one active substance, further comprises 3-(4'-methylbenzylidene)-dl-camphor, 1-(4-tert-butylphenyl)-3-(4-methoxyphenyl)propane-1,3-dione, 2-hydroxy-4-methoxybenzophenone, ethylhexyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid, or a potassium, sodium or triethanolamine salt thereof.

17. A composition according to claim 9, wherein the ratio of the 1,3,4-trihydroxy-2-butanone to flavonoid is 5:1 to 1:2.

18. A composition according to claim 9, wherein the ratio of the self-tanning substance to flavonoid is 2:1.

19. A composition for the preparation of a composition according to claim 9, wherein at least one flavonoid and at least one active substance are mixed successively with a cosmetically or dermatologically suitable vehicle.

20. A method for the protection of skin comprising topically applying a composition according to claim 9.

21. A kit consisting of a two-chamber system with pump device for application of a composition according to claim 9, where the flavonoid and the self-tanning substance and further active substances and assistants are located in two separate chambers and are applied successively to the skin.

22. A composition according to claim 15 wherein said vitamin is vitamin A palmitate, vitamin C and/or a derivative thereof.

23. A method for the protection of body cells against oxidative stress or for reducing skin ageing comprising applying to the skin of a person in need thereof a composition according to claim 15.

24. A method according to claim 1, wherein the flavonoid is rutin, rutin sulfate, troxerutin and/or isoquercetin.

25. A method according to claim 6, wherein the total amount of flavonoid is 0.1 to 5% by weight.

26. A method according to claim 3, wherein the flavonoid is rutin sulfate.

* * * * *

UNITED STATES PATENT AND TRADEMARK OFFICE
CERTIFICATE OF CORRECTION

| | | |
|---|---|---|
| PATENT NO. | : 8,613,910 B2 | Page 1 of 1 |
| APPLICATION NO. | : 11/996846 | |
| DATED | : December 24, 2013 | |
| INVENTOR(S) | : Rudolph et al. | |

It is certified that error appears in the above-identified patent and that said Letters Patent is hereby corrected as shown below:

In the Claims

Column 24, line 19 reads "one or more antioxidant, vitamin, DL-a-tocopherol, toco-" should read -- one or more antioxidant, vitamin, DL-α-tocopherol, toco- --.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,613,910 B2                              Page 1 of 1
APPLICATION NO. : 11/996846
DATED            : December 24, 2013
INVENTOR(S)      : Rudolph et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 682 days.

Signed and Sealed this
Twenty-second Day of September, 2015

Michelle K. Lee
*Director of the United States Patent and Trademark Office*